US006723536B2

(12) United States Patent
Madsen et al.

(10) Patent No.: US 6,723,536 B2
(45) Date of Patent: Apr. 20, 2004

(54) METHOD OF PRODUCING AND PURIFYING ANGIOSTATIN

(75) Inventors: John Madsen, Jefferson, MD (US); Hong Liang, Gaithersburg, MD (US); Kim Lee Sim, Gaithersburg, MD (US); Xinhua Zhou, North Potomac, MD (US); Amy Chang-Murad, DeRidder, LA (US); Renee J. Boerner, Apex, NC (US); Lourdes L. Bermejo, Morrisville, NC (US); Firoz R. Mistry, Chapel Hill, NC (US); Jeffrey L. Schrimsher, Hillsborough, NC (US); Scot R. Shepard, Clayton, NC (US); Jeremy Johnston, Durham, NC (US)

(73) Assignee: EntreMed, Inc., Rockville, MD (US)

( * ) Notice: Subject to any disclaimer, the term of this patent is extended or adjusted under 35 U.S.C. 154(b) by 0 days.

(21) Appl. No.: 09/982,516

(22) Filed: Oct. 18, 2001

(65) Prior Publication Data
US 2003/0104525 A1 Jun. 5, 2003

Related U.S. Application Data

(63) Continuation of application No. PCT/US00/32843, filed on Dec. 4, 2000.
(60) Provisional application No. 60/168,919, filed on Dec. 3, 1999.

(51) Int. Cl.$^7$ ............................................... C12N 15/00
(52) U.S. Cl. ..................... 435/69.1; 530/350; 536/23.1; 435/254.23
(58) Field of Search ................................. 530/427, 344, 530/412, 417, 415, 416; 435/69.1, 69.6, 254.11, 254.23, 320.1, 476

(56) References Cited

U.S. PATENT DOCUMENTS

| 5,733,876 A | | 3/1998 | O'Reilly et al. |
| 5,837,682 A | * | 11/1998 | Folkman et al. ............... 514/12 |
| 5,837,826 A | * | 11/1998 | Flickinger et al. ........... 530/413 |
| 5,861,295 A | * | 1/1999 | Goldstein et al. ............ 435/194 |

FOREIGN PATENT DOCUMENTS

WO     WO 99/35248 B1     7/1999

OTHER PUBLICATIONS

Johansson et al., J. Biotech. 48 (1996) pp. 9–14.*
MacDonald et al., biochemical and Biophysical Research Communications, 264, pp. 469–477 (1999).*
Johansson, H.J., et al., "Large Scale Recovery and Purification of Periplasmic Recombinant Protein from *E.coli* Using Expanded Bed Absorption Chromatography Followed by New Ion Exchange Media", Journal of Biotechnology, vol. 48, 1996, pp. 9–14.
Wu, Zhanggui, et al., "Suppression of Tumor Growth with Recombinant Murine Angiostatin", Biochemical and Biophysical Research Communication, vol. 236, No. 3, 1997, pp. 651–654.
Shepard, Scot R., et al., "Large–Scale Purification of Recombinant Human Angiostatin", Protein Expression and Purification, vol. 20, Nov. 2000, pp. 216–227.

* cited by examiner

*Primary Examiner*—Karen Cochrane Carlson
*Assistant Examiner*—Anand U Desai
(74) *Attorney, Agent, or Firm*—Kilpatrick Stockton LLP

(57) ABSTRACT

The present invention provides a method for recombinant production, recovery and purification of angiostatin protein. This method may be employed for large scale recovery and purification of recombinantly-produced angiostatin protein.

6 Claims, 10 Drawing Sheets

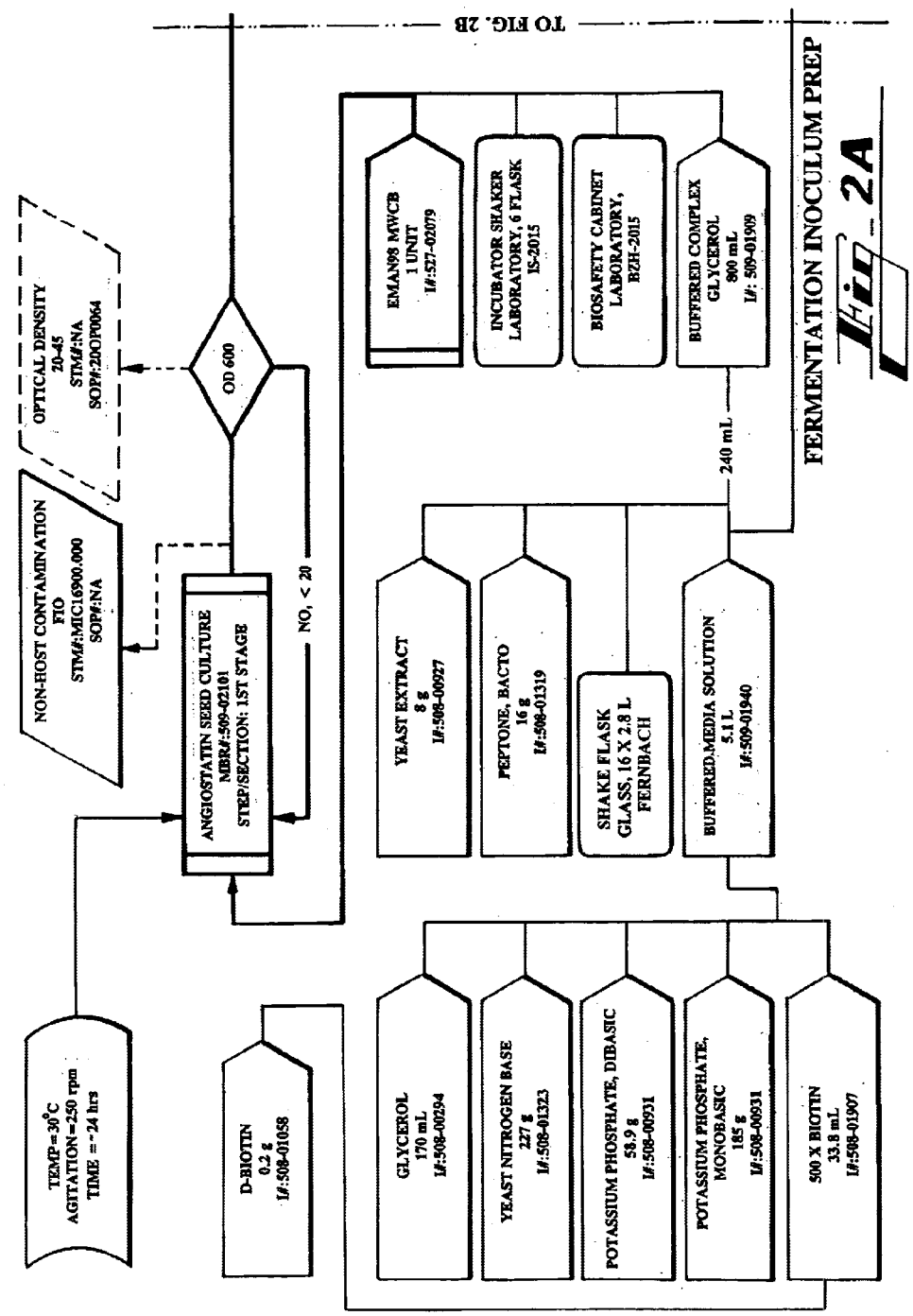

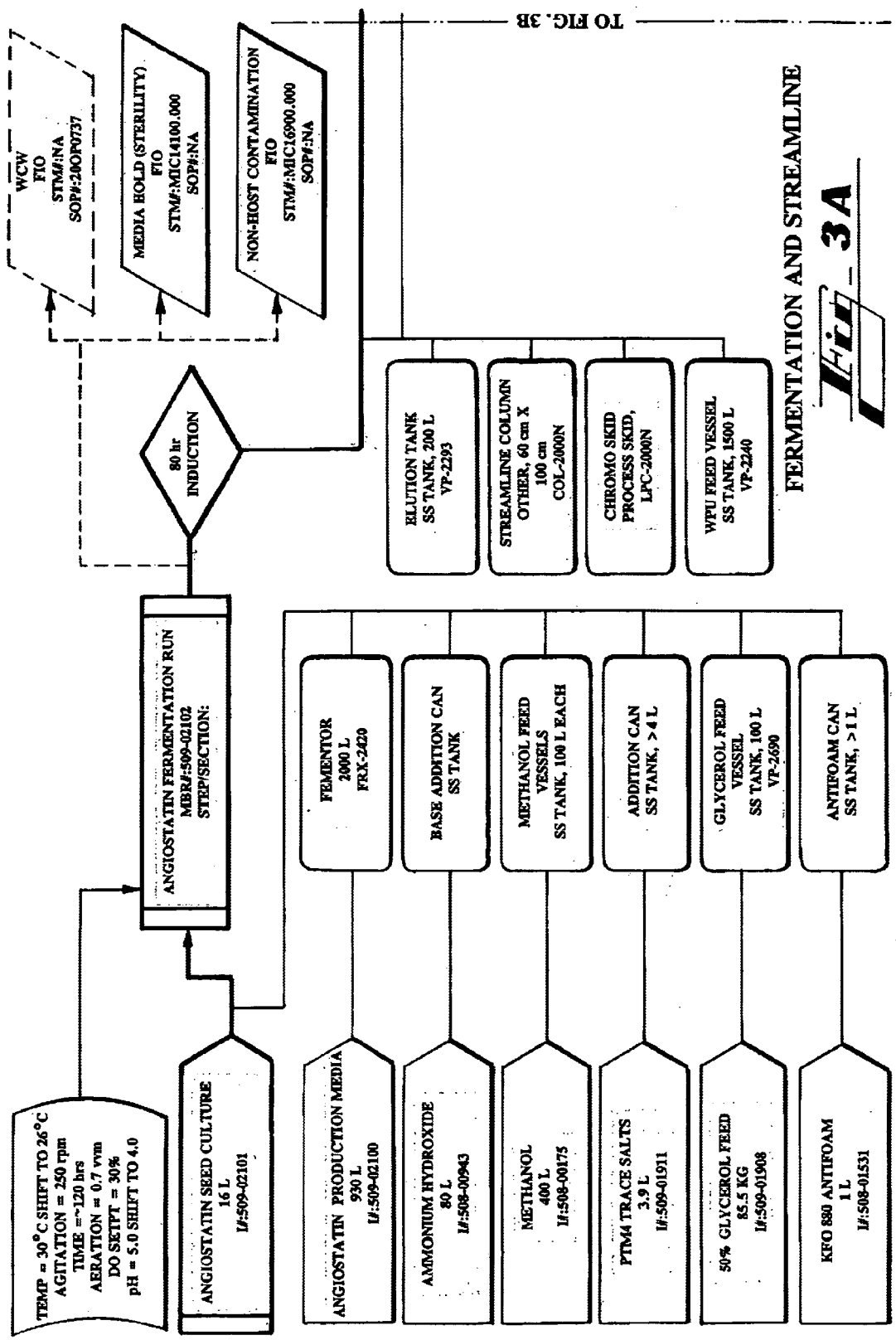

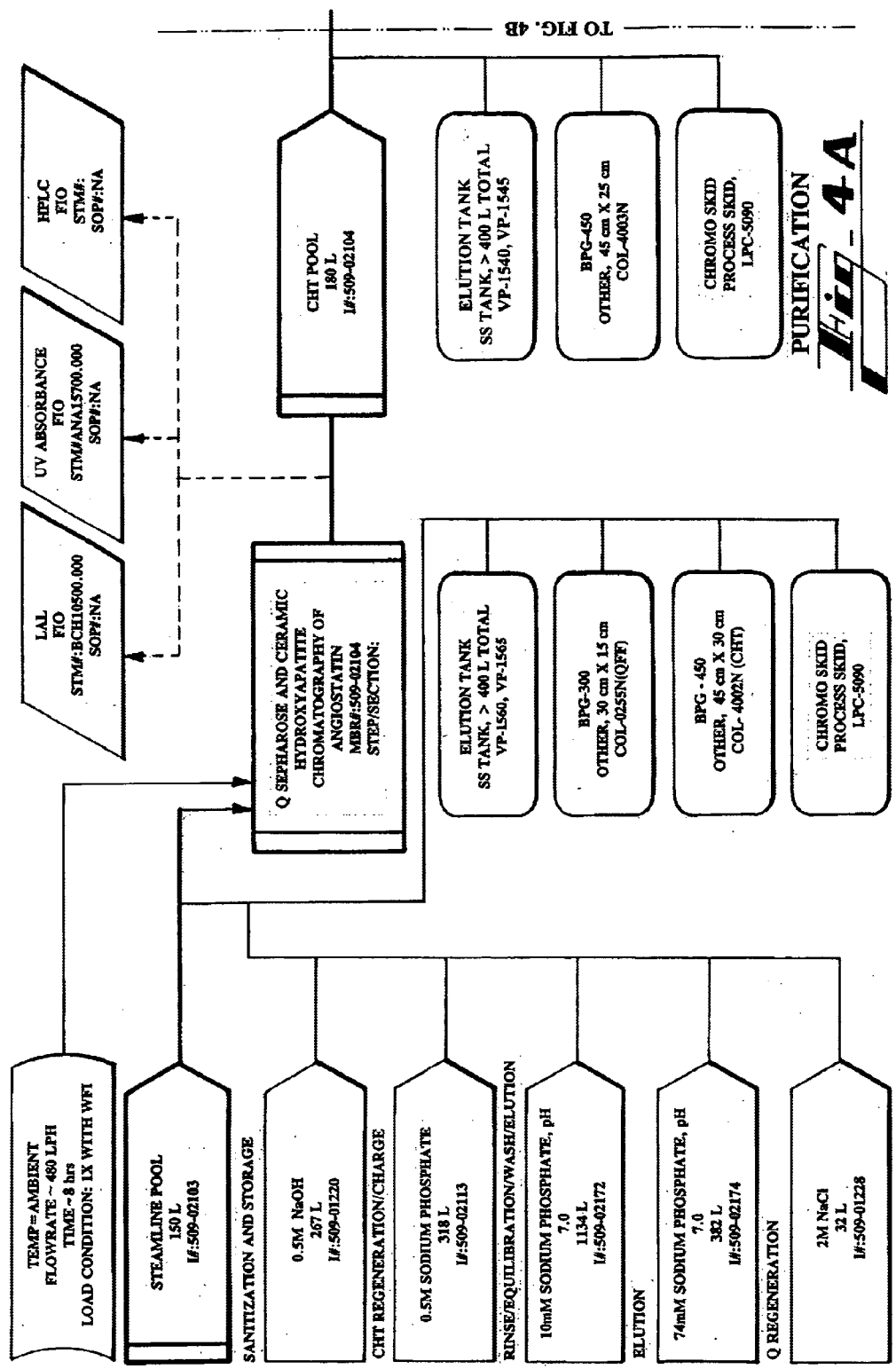

PURIFICATION CONTINUED

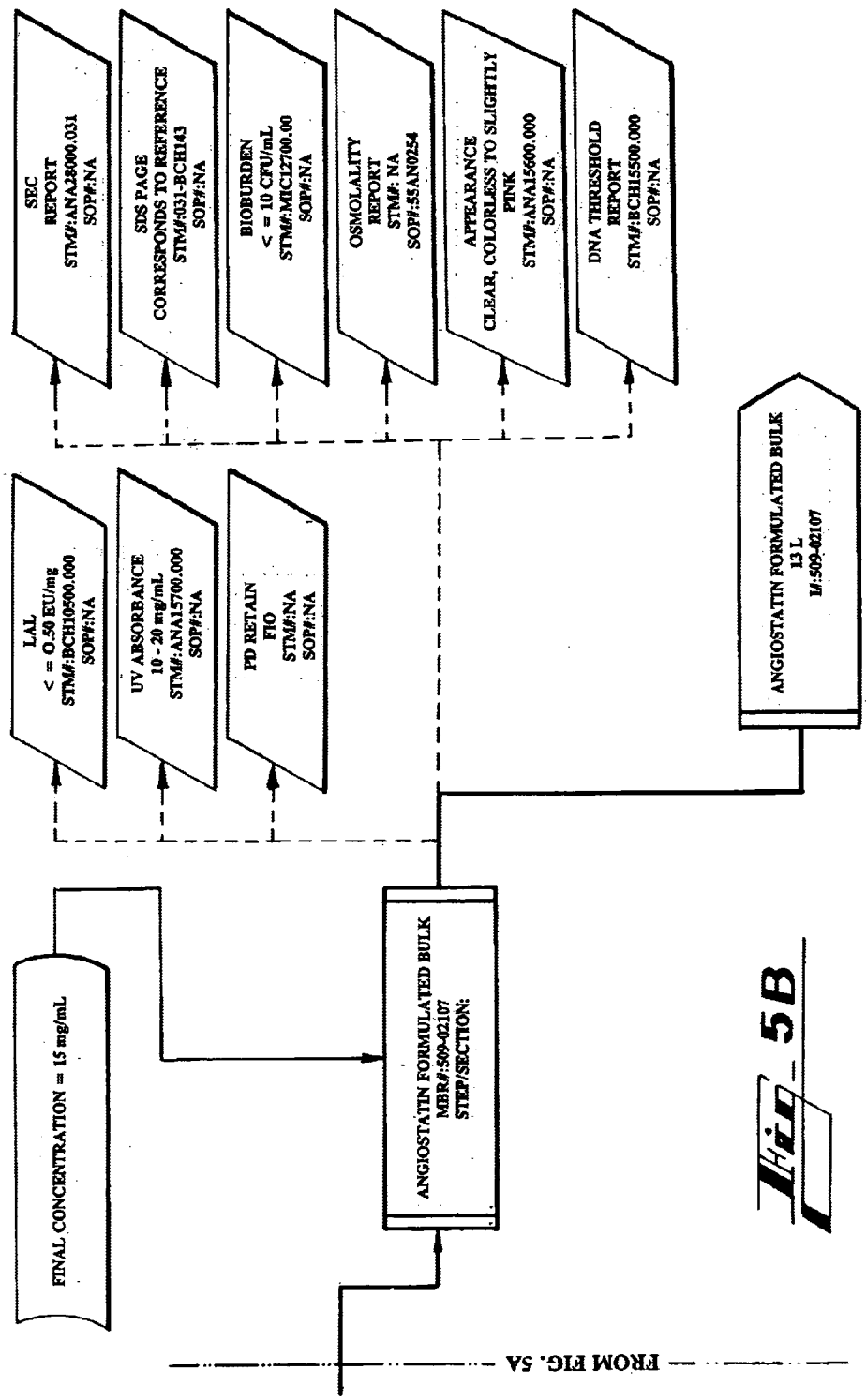

SEQUENCE LISTING

<160> NUMBER OF SEQ ID NOS: 2

<210> SEQ ID NO 1
<211> LENGTH: 260
<212> TYPE: PRT
<213> ORGANISM: Homo sapiens

<400> SEQUENCE: 1

```
Val Tyr Leu Ser Glu Cys Lys Thr Gly Asn Gly Lys Asn Tyr Arg Gly
1               5                   10                  15

Thr Met Ser Lys Thr Lys Asn Gly Ile Thr Cys Gln Lys Trp Ser Ser
            20                  25                  30

Thr Ser Pro His Arg Pro Arg Phe Ser Pro Ala Thr His Pro Ser Glu
        35                  40                  45

Gly Leu Glu Glu Asn Tyr Cys Arg Asn Pro Asp Asn Asp Pro Gln Gly
    50                  55                  60

Pro Trp Cys Tyr Thr Thr Asp Pro Glu Lys Arg Tyr Asp Tyr Cys Asp
65                  70                  75                  80

Ile Leu Glu Cys Glu Glu Glu Cys Met His Cys Ser Gly Glu Asn Tyr
                85                  90                  95

Asp Gly Lys Ile Ser Lys Thr Met Ser Gly Leu Glu Cys Gln Ala Trp
            100                 105                 110

Asp Ser Gln Ser Pro His Ala His Gly Tyr Ile Pro Ser Lys Phe Pro
        115                 120                 125

Asn Lys Asn Leu Lys Lys Asn Tyr Cys Arg Asn Pro Asp Arg Glu Leu
    130                 135                 140

Arg Pro Trp Cys Phe Thr Thr Asp Pro Asn Lys Arg Trp Glu Leu Cys
145                 150                 155                 160

Asp Ile Pro Arg Cys Thr Thr Pro Pro Pro Ser Ser Gly Pro Thr Tyr
                165                 170                 175

Gln Cys Leu Lys Gly Thr Gly Glu Asn Tyr Arg Gly Asn Val Ala Val
            180                 185                 190

Thr Val Ser Gly His Thr Cys Gln His Trp Ser Ala Gln Thr Pro His
        195                 200                 205

Thr His Glu Arg Thr Pro Glu Asn Phe Pro Cys Lys Asn Leu Asp Glu
    210                 215                 220

Asn Tyr Cys Arg Asn Pro Asp Gly Lys Arg Ala Pro Trp Cys His Thr
225                 230                 235                 240

Thr Asn Ser Gln Val Arg Trp Glu Tyr Cys Lys Ile Pro Ser Cys Asp
                245                 250                 255

Ser Ser Pro Val
            260
```

<210> SEQ ID NO 2

-continued

```
<211> LENGTH: 780
<212> TYPE: DNA
<213> ORGANISM: Homo sapiens

<400> SEQUENCE: 2
gtgtatctct cagagtgcaa gactgggaat ggaaagaatt acagagggac gatgtccaaa      60
acaaaaaatg gcatcacctg tcaaaaatgg agttccactt ctccccacag acctagattc     120
tcacctgcta cacacccctc agagggactg gaggagaact actgcaggaa tccagacaac     180
gatccgcagg ggccctggtg ctatactact gatccagaaa agagatatga ctactgcgac     240
attcttgagt gtgaagagga atgtatgcat tgcagtggag aaaactatga cggcaaaatt     300
tccaagacca tgtctggact ggaatgccag gcctgggact ctcagagccc acacgctcat     360
ggatacattc cttccaaatt tccaaacaag aacctgaaga agaattactg tcgtaacccc     420
gatagggagc tgcggccttg gtgtttcacc accgacccca acaagcgctg ggaactttgt     480
gacatccccc gctgcacaac acctccacca tcttctggtc ccacctacca gtgtctgaag     540
ggaacaggtg aaaactatcg cgggaatgtg gctgttaccg tgtccgggca cacctgtcag     600
cactggagtg cacagacccc tcacacacat gaaaggacac cagaaaactt ccctgcaaa     660 aatttggatg aaaactactg ccgcaatcct gacggaaaaa gggcccatg gtgccataca     720 accaacagcc aagtgcggtg ggagtactgt aagataccgt cctgtgactc ctccccagta     780
```

METHOD OF PRODUCING AND PURIFYING ANGIOSTATIN

PRIORITY DATA

This application is a continuation of PCT/US00/32843, filed Dec. 4,2000 and provisional application Ser. No. 60/168,919, filed Dec. 3, 1999.

FIELD OF THE PRESENT INVENTION

The present invention relates to a novel method of recombinantly producing, recovering and purifying angiostatin protein (EntreMed Inc., Rockville, Md.).

BACKGROUND OF THE INVENTION

Angiostatin is a protein which is a potent inhibitor of developing blood vessels and tumor growth. Angiostatin is believed to play an important role in the inhibition of the development of blood vessels to new tumor metastases.

Isolation and purification of proteins, such as angiostatin protein, in high yield from biological material, such as tissue extracts, cell extracts, broth from incubation systems, and culture medium is often frought with problems in view of the numerous proteins and other undesirable molecules present in an homogenate or extract. What is needed are recombinant methods of producing angiostatin protein that will provide the large amounts of angiostatin protein required for clinical use, including, but not limited to, cancer therapy. Such methods should produce angiostatin protein in an efficient and convenient manner in a culture broth which is amenable to procedures designed to recover and purify angiostatin protein in high yields. Separating a, specific protein of interest from potential contaminants presents a challenge in view of numerous factors, such as contamination of cellular homogenates with proteolytic enzymes that may digest the protein. Other undesirable cellular constituents that may be present in homogenates, include but not limited to, pigments, cytochromes, lipids, free radicals, oxidases and other lysosomal enzymes, and oxides. Some of these substances may affect the protein of interest by stripping electrons, affecting disulfide bonds and changing the conformation of the protein.

Centrifugation of cells, including yeast, bacteria, insect and other cells used for recombinant production of proteins, such as angiostatin protein, could possibly result in damage to the cells with concomitant release of undesirable biological material. What is needed is a method for recovery and purification of protein, such as angiostatin protein, which does not employ centrifugation.

Methods for recombinant production, recovery and purification of angiostatin protein on a large scale are required to produce and isolate the amounts of purified angiostatin protein needed for administration to patients and also for research purposes.

Also needed is a method for purifying recombinantly-produced angiostatin protein which avoids the need for centrifugation of the culture broth, thereby avoiding problems associated with cell lysis. This method should be capable of use on a large scale to recover and purify angiostatin protein in quantities needed for clinical administration and research.

What is also needed is a method for purifying recombinantly produced angiostatin protein which minimizes contamination with cytochromes, pigments, enzymes, and other undesirable cellular constituents.

Also needed are solutions for storage of angiostatin protein following the recovery and purification process which optimizes solubility properties of angiostatin protein.

SUMMARY OF THE INVENTION

The present invention solves these problems inherent in the recovery and purification of proteins, particularly angiostatin protein, by providing new and useful methods for recombinant production, recovery and purification of proteins, especially angiostatin protein. The present invention provides new and useful methods for recombinantly producing angiostatin protein in large amounts. The present invention provides a method for recovery and purification of angiostatin protein. The present invention also provides new and useful solutions for storage of angiostatin protein. These methods provide the benefit of preserving the biological activity of angiostatin protein. Preservation of the biological activity of angiostatin protein is crucial for administration of angiostatin protein to humans and animals for the purpose of inhibition of undesirable angiogenesis, for other biological activities, and for research investigations or other types of biological testing.

Angiostatin protein is effective in treating diseases or processes that are mediated by, or involve, angiogenesis. The angiogenesis mediated diseases include, but are not limited to, solid tumors; blood born tumors such as solid tumors, blood borne tumors, leukemias; tumor metastases; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, colon cancer, retrolental fibroplasia, rubeosis; Osler-Webber Syndrome; myocardial angiogenesis; plaque neovascularization; telangiectasia; hemophiliac joints; angiofibroma; and wound granulation.

In one embodiment, the present invention provides new and improved methods for recombinant production of biologically active angiostatin protein in high yield.

In another embodiment, the method of the present invention is useful for recovery and purification of recombinantly-produced angiostatin protein.

In another embodiment, the method of the present invention is useful for recovery and purification of angiostatin protein from extracts of biological fluids, cells and tissues.

An advantage of the present invention is that higher amounts of biologically active angiostatin protein are recombinantly produced. Another advantage of the present invention is that greater amounts of angiostatin protein are recovered than obtained with prior art methods. Yet another advantage of the present invention is that higher yields of more purified, and biologically active angiostatin protein are obtained. Still another advantage of the present invention is that angiostatin protein may be stored in buffers for extended periods of time, and also subjected to lyophilization, while preserving biological activity. An advantage of the present invention is that it permits angiostatin protein to be stored in vials or other containers, either in a solution which may be liquid or frozen, or lyophilized, and optionally shipped to a recipient.

Accordingly, an object of the present invention is to provide an improved method for recombinant production of large amounts of biologically active angiostatin protein.

Another object of the present invention is to provide a method for recovery and purification of recombinantly produced proteins.

Yet another object of the present invention is to provide a method for recovery and purification of angiostatin protein.

Another object of the present invention is to provide a method for recovery and purification of angiostatin protein, particularly recombinantly produced angiostatin protein.

An advantage of the purification methods of the present invention is that undesirable proteins, lipids and pigments are efficiently separated from the desired protein, especially angiostatin protein.

It is another object of the present invention to provide solutions which provide favorable solubility conditions for angiostatin protein, particularly recombinantly-produced angiostatin protein while retaining biological activity of angiostatin protein.

Another advantage of the methods of the present invention is that centrifugation of the broth from fermentation steps in recombinant production of angiostatin protein is avoided, thereby preventing unwanted cellular lysis and potential contamination of angiostatin protein with additional proteins, pigments, enzymes and other cellular chemicals and debris.

Another object of the present invention is to provide methods amenable to large scale production, recovery and purification of recombinantly-produced angiostatin protein.

Another advantage of the present invention is that the recovered and purified angiostatin protein is provided in a solution which optimizes solubility of angiostatin protein, while preserving the bioactivity of angiostatin protein.

These and other objects, features and advantages of the present invention will become apparent after a review of the following detailed description.

DETAILED DESCRIPTION

Figure 1:
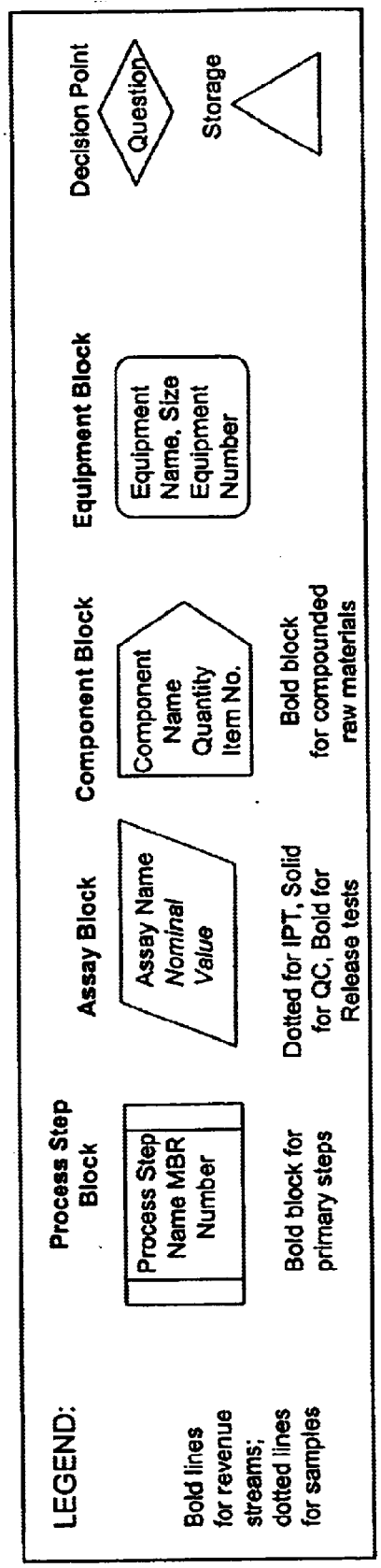
FIG. 1 is a process overview diagram for the large scale processing of purified angiostatin protein.
Figure 1B:
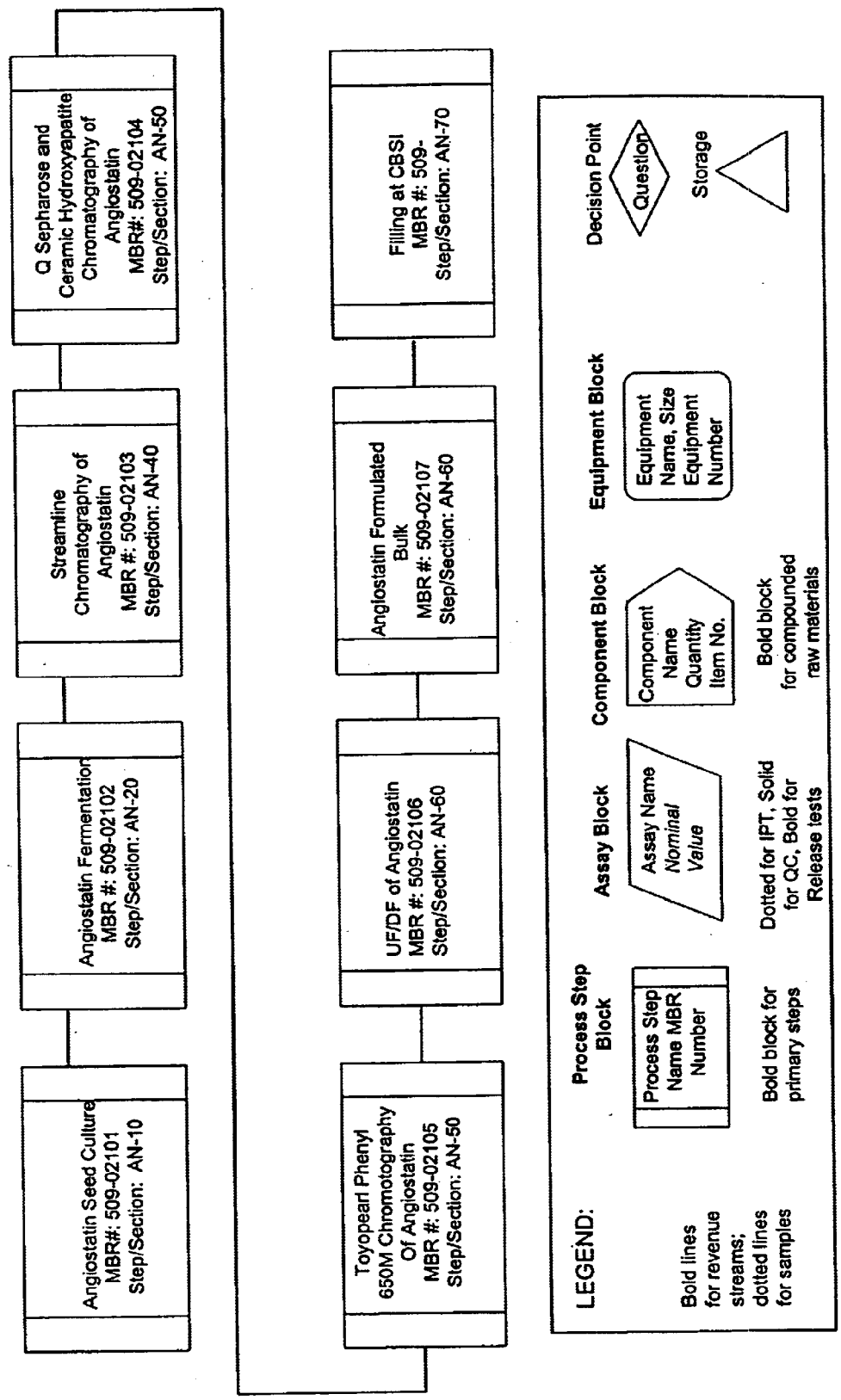
Figure 2B:
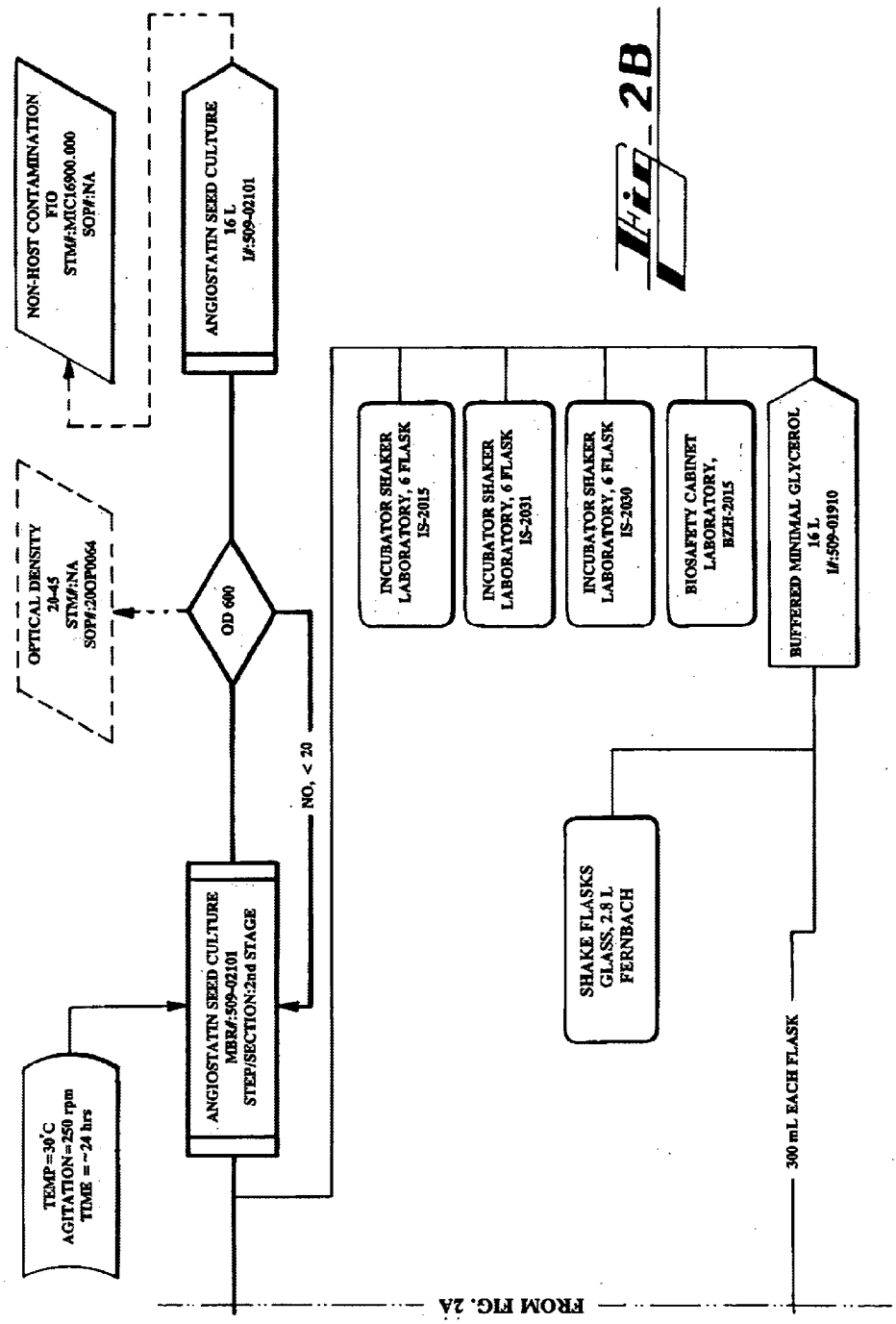
FIG. 2 is a process flow diagram for fermentation inoculum preparation for angiostatin production.
Figure 3B:
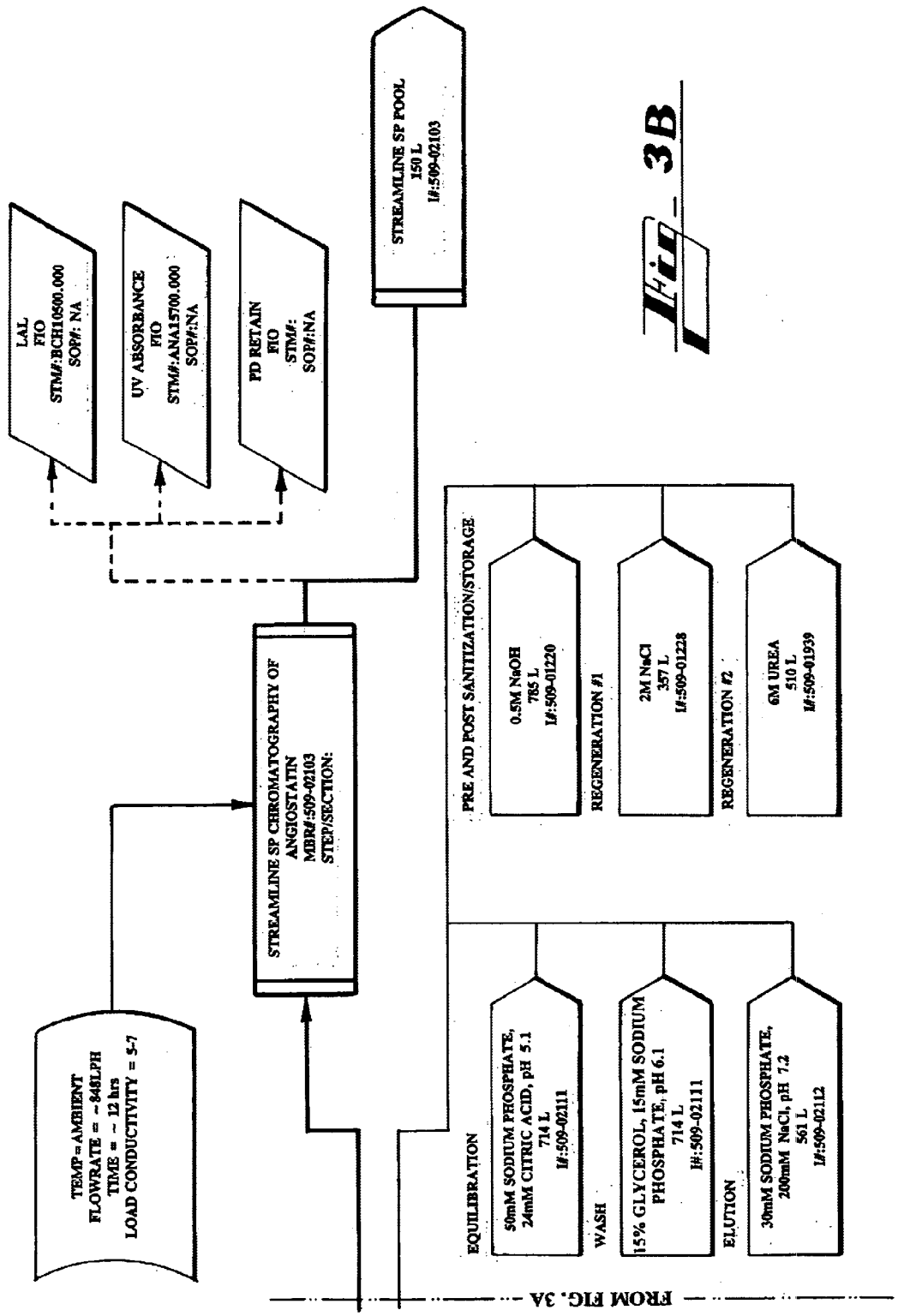
FIG. 3 is a process flow diagram for fermentation and STREAMLINE® SP chromatography (cation-exchange resin) for angiostatin production.
Figure 4B:
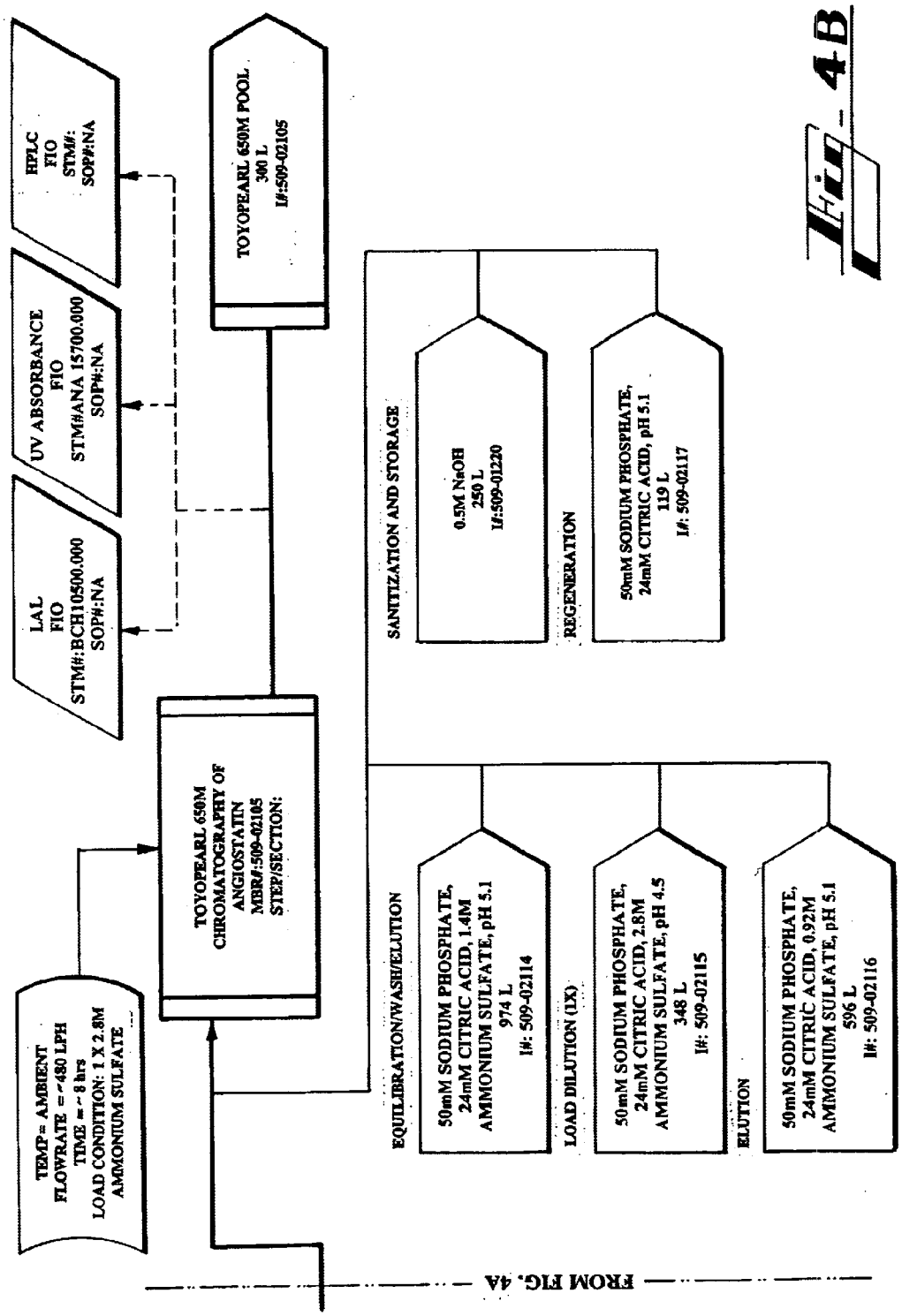
FIG. 4 is a process flow diagram for chromatography steps following STREAMLINE® SP chromatography (cation-exchange resin) for angiostatin production.
Figure 5A:
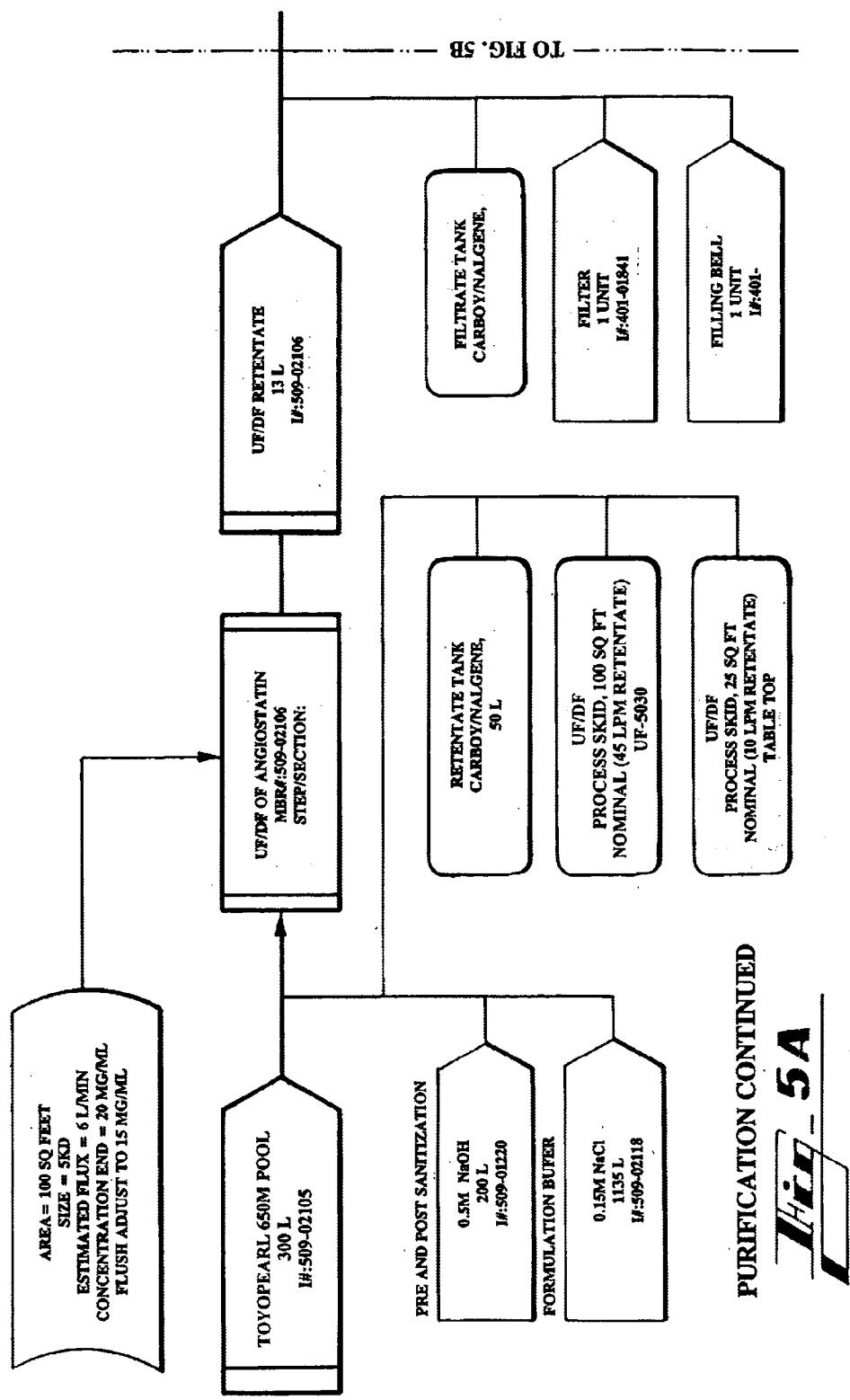
FIG. 5 is a process flow diagram for chromatography, ultrafiltration, diafiltration and formulated bulk processing steps following TOYOPEARL® (hydrophobic interaction resin) chromatography for angiostatin production.

Angiostatin is a protein which is a potent inhibitor of developing blood vessels and tumor growth. Angiostatin is believed to play an important role in the inhibition of the development of blood vessels to new tumor metastases. The following pages of this patent application describe new procedures and protocols for the large scale production of human recombinant angiostatin from *Pichia pastoris* fermentation of clones with nucleic acid sequences encoding for angiostatin protein or variants thereof. This application also provides new procedures for the large scale production, purification, characterization and storage of human recombinant angiostatin. It is to be understood that the methods of the present invention are not limited to human recombinant angiostatin, and that the present methods apply to angiostatin from other species, as well as fragments and conservatively substituted forms thereof.

The method can serve as a large scale purification protocol for obtaining angiostatin formulations which may be used in clinical human trials.

Definitions

Definitions for other terms used herein are as follows. The terms "a", "an" and "the" as used herein are defined to mean "one or more" and include the plural unless the context is inappropriate. As used herein, the terms "detecting" or "detection" refer to qualitatively or quantitatively determining the presence of a molecule under investigation.

"Proteins", "peptides", "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the peptide, or to the alpha-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

Typically, the amino acids making up a peptide are numbered in order, starting at the amino terminal and increasing in the direction toward the carboxy terminal of the peptide. Thus, when one amino acid is said to "follow" another, that amino acid is positioned closer to the carboxy terminal of the peptide than the preceding amino acid.

The term "residue" is used herein to refer to an amino acid (D or L) or an amino acid mimetic that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

The term "angiostatin protein" refers to proteins that may be synthesized and may be isolated from biological tissues, cells, cell culture medium, and from broth and media obtained from cellular and cell-free expression systems. Accordingly, the term angiostatin protein includes angiostatin protein produced from recombinant expression systems. The term angiostatin protein also includes precursor forms of the angiostatin protein. The term angiostatin protein also includes fragments of the protein, and modified proteins and peptides thereof that have a substantially similar amino acid sequence, and that are capable of inhibiting proliferation of proliferation of blood vessels. For example, silent substitutions of amino acids, wherein the replacement of an amino acid with a structurally or chemically similar amino acid does not significantly alter the structure, conformation or activity of the protein, are well known in the art. Such silent substitutions are intended to fall within the scope of the present invention. The term angiostatin protein also includes various post-translational modifications or other modifications of angiostatin protein, including, but not limited to, phosphorylation, glycosylation, sulfation, and disulfide bond formation or reduction.

It will be appreciated that the term angiostatin protein, as used herein, includes shortened proteins or peptide fragments of angiostatin protein wherein one or more amino acids, preferably 1 to 10 amino acids, are removed from either or both ends of angiostatin protein, or from an internal region of the protein, yet the resulting molecule retains bioactivity such as inhibiting proliferation of blood vessels. The term angiostatin protein also includes lengthened proteins or peptides wherein one or more amino acids, preferably 1 to 10 amino acids, is added to either or both ends of angiostatin protein, or to an internal location in the angiostatin protein, yet the resulting molecule retains the ability to inhibit proliferation of blood vessels.

Also included in the definition of the term angiostatin protein are modifications of the angiostatin protein, its subunits and peptide fragments. Such modifications include substitutions of naturally occurring amino acids at specific sites with other molecules, including but not limited to naturally and non-naturally occurring amino acids. Such substitutions may modify the bioactivity of angiostatin protein and produce biological or pharmacological agonists or antagonists. Such substitutions may include conservative substitutions known to one of skill in the art, such as valine for alanine. Acceptable substitutions may also include modifications of amino acids, such as norleucine for leucine. It is to be understood that substitution of D amino acids for L amino acids is encompassed within the scope of the present invention. Some substitutions are described in *Dictionary of Biochemistry and Molecular* Biology, 2"a ed., J. Stenesh, John Wiley & Sons, 1989, the entirety of which is incorporated herein by reference. Additional modifications include addition of an amino acid, such as a tyrosine or another amino acid at specific locations in angiostatin protein or fragments thereof to enhance labeling potential with radioactive and non-radioactive labels, addition of molecules such as ricin, addition of radioactive and/or nonradioactive labels.

"Substantial sequence homology" means at least approximately 70% homology between the acid residue sequence in the angiostatin protein analog sequence and that of angiostatin protein, preferably at least approximately 80% homology, more preferably at least approximately 90% homology.

Furthermore, one of skill in the art will recognize that individual substitutions, deletions or additions in the amino acid sequence of angiostatin protein, or in the nucleotide sequence encoding for the amino acids in the angiostatin protein, which alter, add or delete a single amino acid or a small percentage of amino acids (typically less than 5%, more typically less than 1%) in an encoded sequence are conservatively modified variations, wherein the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q;
4) Arginine (R), Lysine (K);
5) Isoleucine (I), Leucine (L), Methionine (M); Valine (V); and
6) Phenylalanine (F), Tyrosine (Y), Tryptophan (W).

Methods of Producing Angiostatin Protein

Angiostatin protein can be isolated from biological sources, including tissues, cells and biological fluids. Angiostatin protein may be produced from recombinant sources, from genetically altered cells implanted into animals, from tumors, and from cell cultures, as well as other sources. Angiostatin protein can be isolated from body fluids including, but not limited to, serum, urine and ascites, or synthesized by chemical or biological methods (e.g. cell culture, recombinant gene expression, cellular and cell free expression systems, peptide synthesis, and in vitro and in vivo enzymatic catalysis of precursor molecules to yield active angiostatin protein). Recombinant techniques include gene amplification from DNA sources using the polymerase chain reaction (PCR), and gene amplification from RNA sources using reverse transcriptase/PCR.

Angiostatin protein can be made by automated protein synthesis methodologies well known to one skilled in the art. Alternatively, angiostatin protein may be isolated from larger known proteins. Angiostatin protein can also be produced synthetically by chemical reaction or by recombinant techniques in conjunction with expression systems.

It is contemplated as part of the present invention that angiostatin protein can be isolated from a body fluid such as blood or urine of patients. Angiostatin protein can also be produced by recombinant DNA methods or synthetic peptide chemical methods that are well known to those of ordinary skill in the art. In a preferred embodiment of the present invention, angiostatin protein is recombinantly produced. A preferred method of recombinant production of angiostatin protein is a method employing *Pichia pastoris*. Novel methods of isolation and purification of angiostatin protein, especially recombinantly-produced angiostatin protein are provided in the present invention.

It is to be understood that a variety of expression systems may be used for recombinant production of angiostatin protein. These expression systems include, but are not limited to *Pichia pastoris*, yeast, *E. coli*, insect cells, baculovirus expressions systems, expression in transgenic animals, expression in transgenic plants, mammalian systems, and other systems commonly known to one of ordinary skill in the art of expressing proteins. Some of these expression systems are described in U.S. Pat. No. 5,854,205. Although the *Pichia pastoris* expression system was used for most of the recombinant angiostatin protein production presented in the present application, it is to be understood that the present invention encompasses other systems for recombinant production of angiostatin protein. Accordingly, modifications of the angiostatin protein production parameters presented herein can be made by one of ordinary skill in the art of recombinant production of proteins using specific expression systems. For example, when yeast are used for recombinant production of angiostatin protein, different induction methods may be used, as commonly known to one of skill in the art. Yeast can be induced on methanol, or a mixture of methanol and glycerol, all optionally diluted with water, at feed rates commonly known to one of ordinary skill in the use of yeast expression systems for recombinant production of molecules, including proteins.

Culture Conditions

The following description of a preferred embodiment of the culture conditions for angiostatin protein is not limiting to the invention, and it is to be understood that the conditions, described here and in the examples may be scaled up or down to accommodate higher or lower requirements for production of angiostatin protein. These conditions may be scaled up to accommodate angiostatin protein production by 5, 10, 20 or 100 fold. It is also to be understood that the various concentrations of solutions and reagents described herein, including description contained in the Tables) are not limiting and may be increased or decreased in a range of 0 to 20%, preferably 0 to 10%, without altering the spirit and scope of the present invention.

Seed Culture

Inoculum cultures are prepared using a two stage seed process of *Pichia pastoris*. The first stage employs an enriched media (about 800 mL in a 2.8 l, flask) and is incubated at 250 rpm and about 30° C. for approximately 24 hours to a final optical density at 600 nm ($OD_{600\,nm}$) of greater than 30. The second stage uses a similar media base (16×1L in 2.8L shaker flasks) and is incubated at about 250 rpm and 30° C. for approximately 16 hours to a final $OD_{600\,nm}$ of between about 20.0 and 30.0.

Main Fermentation

The fermentation media consists of Calcium Sulfate, Potassium Sulfate, Magnesium Sulfate, Potassium Hydroxide, Phosphoric Acid and Glycerol. Post sterilization addition of Trace Salts Solution is necessary. The fermentation consists of four main phases; batch glycerol, fed-batch glycerol, methanol ramp and methanol soak.

The batch glycerol phase is the beginning phase which utilizes the initial charge of Glycerol as the carbon source. This phase lasts for approximately 30 hours. A sharp DO spike characterizes the end of this phase. The spike indicates the depletion of the carbon source.

The fed-batch glycerol phase is initiated at a set flow (16.1 g/Kg/hr) immediately following the batch glycerol phase. The fed-batch glycerol phase lasts for 6 hours. During the final two hours of the fed-batch phase, the pH is allowed to decrease from 5.0 to 4.0. The temperature is also decreased from 30° C. to 26° C. during the last two hours of the phase. The methanol ramp phase is initiated immediately following the fed-batch glycerol phase. The methanol is used as a carbon source and as a product inducer. Angiostatin is produced as a secreted protein. During this phase, the methanol flowrate to the fermentor is ramped linearly from 1.5 to 4.5 mL/Kg/hr at a rate of 1.0 mL/Kg/hr$^2$.

The final phase of the fermentation is the methanol induction phase. The methanol continues to be used as a carbon source and product inducer. During this phase the methanol is fed to the fermentor at a set rate of 4.5 mL/Kg/hr for—83 hours. Harvest conditions are then set, after the conditions have been achieved the fermentation process is ready for harvest. To minimize foaming, the methanol and pH loops are not shutoff until the temperature is below 20° C. Final angiostatin concentration is approximately 500 mg/L in the supernatant. The final WCW is approximately 300 g/L.

Many of the solutions and other conditions used in the incubation are shown in the following tables. It is to be understood that these conditions are not limiting, and that they may be increased or decreased to accommodate scale up or scale down of the procedure to attain a desired production level of angiostatin protein.

Process Data Sheets
Fermentation

| | | |
|---|---|---|
| Seed Culture 1st Stage | | |
| Media Components/ Concentration: | Biotin | 0.4 mg/L |
| | Glycerol | 10 g/L |
| | Yeast Nitrogen Base | 13.4 g/L |
| | Peptone | 20 g/L |
| | Yeast Extract | 10 g/L |
| | Potassium Phosphate Monobasic | 10.9 g/L |
| | Potassium Phosphate Dibasic | 3.5 g/L |
| Shake Volume: | 800 mL | |
| Inoculum Size: | 1.0 mL | |

-continued

Process Data Sheets
Fermentation

| | | |
|---|---|---|
| Incubation Conditions: | 250 rpm and 30° C. | |
| Incubation End Conditions: | OD600 nm 20–30 (approximately 24 hours) | |
| 2$^{nd}$ Stage | | |
| Media Components/ Concentration: | Biotin | 0.4 mg/L |
| | Glycerol | 10 g/L |
| | Yeast Nitrogen Base | 13.4 g/L |
| | Potassium Phosphate Monobasic | 10.9 g/L |
| | Potassium Phosphate Dibasic | 3.5 g/L |
| Shake Volume: | 16 × 1L | |
| Inoculum Size: | Such that initial OD600 nm = 0.85 ± 0.15 | |
| Incubation Conditions: | 250 rpm and 30° C. | |
| Incubation End Conditions: | OD600 nm 6.0–12.0 (approximately 16 hours) | |
| Testing: Fermentation Pre Inoculum Specifications | Non-host Contamination | |
| Media Components/ Concentration: | Calcium Sulfate, dihydrate ($CaSO_4*2H_2O$) | 0.93 g/L |
| | | 18.2 g/L |
| | Potassium Sulfate ($K_2SO_4$) | 14.9 g/L |
| | Magnesium Sulfate ($MgSO_4*7H_2O$) | 4.13 g/L |
| | Potassium Hydroxide (KOH) | 26.7 mL/L |
| | Phosphoric Acid ($H_3PO_4$) | 40 mL/L |
| Density: | Glycerol | |
| Pre SIP Volume: | 1.05 Kg/L | |
| Post SIP Volume: | 900 L (945 Kg) | |
| (Calculations based on Post SIP Volume): | 927 L (973 Kg) | |
| Sterile Additions: | PTM$_4$ Trace Salts | 4.0 mL/L |
| Antifoam: | KFO 880 ~2 L required | |
| Testing: | Media Hold (sterility) | |
| PTM$_4$ Solution | | |
| Component and Concentration: | Cupric Sulfate ($CuSO_4*5H_2O$) | 2 g/L |
| | Sodium Iodide (NaI) | 0.08 g/L |
| | Manganese Sulfate ($MnSO_4*H_2O$) | 3 g/L |
| | Sodium Molybdate ($Na_2MoO_4*2H_2O$) | 0.2 g/L |
| | Boric Acid ($H_3BO_3$) | 0.02 g/L |
| | Cobalt Chloride ($CoCl_2*6H_2O$) | 0.5 g/L |
| | Zinc Chloride ($ZnCl_2$) | 7 g/L |
| | Ferric Sulfate ($FeSO_4*7H_2O$) | 22 g/L |
| | d-Biotin | 0.2 g/L |
| | Sulfuric Acid ($H_2SO_4$) | 1 ML/L |
| Batch Glycerol Phase and Fermentation Conditions | | |
| Carbon Source: | Initial Charge of Glycerol | |
| Temperature: | 30° C. | |
| pH: | 5.0 | |
| Agitation: | 250 rpm | |
| Aeration: | 0.666 vvm (per Post SIP weight) = 650 slpm | |
| DO: | 30% (controlled by oxygen supplementation) | |
| Back-pressure: | 3 psig | |
| In Process Testing: | Wet Cell Weight, OD600 nm, offline pH, and methanol concentration | |
| Fed-Batch Glycerol Phase | | |
| Purpose: | Expansion of cell density | |
| Start: | Approximately fermentation hour 30 | |
| Flowrate: | 16.6 g/Kg/hr (per Kg of Post SIP weight) | |
| Duration: | 6 hours | |
| Glycerol Specifics: | 50% Glycerol Solution (by weight) with KFO 880 Antifoam (0.2 mL/Kg) | |
| pH Shift Start: | 4$^{th}$ hour of Fed Batch Glycerol | |
| pH Shift | Linear Decrease from 5.0 to 4.0 | |

-continued

Process Data Sheets
Fermentation

| Specifics: | |
|---|---|
| pH Shift Duration: | 2 hours |
| Temperature Shift Start: | 4th hour of Fed Batch Glycerol |
| Temperature Shift Specifics: | Linear Decrease from 30° C. to 26° C. |
| Temperature Shift Duration: | 2 hours |
| Methanol Adaptation Phase | |
| Purpose: | Methanol as inducer and carbon source |
| Start: | Immediately following Fed-Batch Glycerol Phase |
| Initial Flowrate: | 1.5 mL/Kg/hr (per Kg of Post SIP weight) |
| Final Flowrate: | 4.5 mL/Kg/hr (per Kg of Post SIP weight) |
| Ramp Rate: | 1.0 mL/Kg/hr2 (~3 hours) |
| Methanol Induction Phase | |
| Start: | Immediately following Methanol Ramp Phase |
| Flowrate: | 4.5 mL/Kg/hr (per Kg of Post SIP weight) |
| Duration: | 83 hours |
| Soak specifics: | Oxygen consumption ~ Unknown at this time slpm/Kg (per Kg of Post SIP weight) |
| Harvest Conditions and Specifics | |
| Temperature: | 10° C. |
| Agitation: | 50 rpm (250 rpm until 20° C. is reached) |
| Aeration: | 50 slpm (650 slpm until 20° C. is reached) |
| DO Control: | OFF |
| Back-pressure: | 3 psig |
| Specifics: | pH loop ON until <20° C. is met Methanol flowrate reduced to 2.1 mL/Kg/hr, turned off when 20° C. met Angiostatin Concentration ~0.5 mg/L in supernatant Final Weight of ~1450 Kg Final WCW of ~300 g/L |
| QC Testing: | Non-Host Contamination |

Method for Isolation and Purification of Angiostatin Protein

The present invention also provides a new and useful method for recovery and purification of proteins, particularly recombinantly-produced proteins. The methods of the present invention may be used for recovery and purification of angiostatin protein from biological sources, including but not limited to biological fluids, tissues, cells, culture media, and fermentation media. In one embodiment, the present invention provides a new and useful method for recovery and purification of angiostatin protein, and more particularly, recombinantly-produced angiostatin protein. This method may be employed for large scale recovery and purification of recombinantly-produced angiostatin protein. It is to be understood that the present invention is useful for recovery and purification of angiostatin protein from any expression system.

The basic recovery process of angiostatin protein is accomplished using four chromatography steps and a final concentration and diafiltration step. These steps are shown schematically in FIGS. 1 through 5. FIG. 1 presents an overview of the process.

Upon completion of fermentation, the broth, which consists of all components (cells, nutrients, and buffer) within the fermenter, is diluted with water to a conductivity that favors binding of the target protein to the first column in the process.

The first chromatography step in the recovery and purification procedure is called the angiostatin protein purification capture step, and the specific resin used is called STREAMLINE®-SP (Pharmacia, Inc.). SP refers to the sulfopropyl functional groups that are attached to the support bead that give the resin its cationic character. It is to be understood that besides STREAMLINE®-SP resin, other resins that act as cation exchangers may be used in the practice of the present invention. Such cation exchangers include but are not limited to carboxymethylcellulose. STREAMLINE® refers to a relatively new format of chromatography that is designed to capture and separate target protein from a milieu of broth, thus eliminating the need for centrifugation to separate cells from the protein-containing supernatant. This type of chromatography is also known as expanded bed absorption chromatography (EBA). In practice, the broth is typically pumped up into a STREAMLINE® column containing about 20–30% by volume of settled resin and approximately 70–80% buffer. As the broth enters the column, the bed of resin expends and flows up, thereby accounting for the name EBA. As the bed flows up, protein is bound to the beads, which can only flow up a finite distance, to an equilibrium level. The cells and non-bound protein however, flow up and out of the column to waste. Once all the broth has been pumped onto and traversed the column, the flow direction is reversed (now in the download direction) and the resin is allowed to pack. What remains is a functional column that can be washed and eluted in the more conventional sense. Angiostatin protein is eluted from this column with salt, and is ready for the next chromatographic step.

The next chromatographic steps in the process are the Q SEPHAROSE® (ion exchange) and hydroxyapatite chromatography columns. These steps are followed by the phenyl column as shown in the figures.

The final step in the purification procedure involved concentration and dialysis using the approach of Ultrafiltration/Diafiltration (UF/DF). In this step, the sample from the preceding step is pushed through a membrane, preferably made from polyethersulfone, with a molecular cutoff chosen to retain angiostatin protein or another protein of interest on the membrane. A preferred molecular cutoff for angiostatin protein is about 3 kDa. Several liters of formulation buffer are run over the membrane to recover retain angiostatin protein, or another protein of interest remaining in the filters. This material recovered from the filters is added to the pool of angiostatin protein. In another embodiment of the present invention, parallel flow concentrators employing porous tubes may be used instead of flat membranes for concentration and dialysis.

The following paragraphs describe the chromatography steps in greater detail.

STREAMLINE® SP Chromatography (cation-exchange resin)

The expanded bed column (60 cm ×18 cm (settled height), 51L of STREAMLINE® SP Resin, expanded bed volume ~150L, expanded bed height of ~54 cm at 300 cm/hr) is sanitized with 0.5M NaOH (held for a minimum of 6 hours). The column is rinsed with WPU until neutral conditions are met.

The column is equilibrated with 50 mM Sodium Phosphate, 24 mM Citric Acid, pH 5.1 until the pH and conductivity of the column are that of the buffer. The angiostatin Fermentation is loaded onto the column while performing inline dilution with WPU to maintain a load conductivity of 9–12 mS/cm. The column is washed with 15% Glycerol, 15 mM Sodium Phosphate, pH 6.1.

The angiostatin is eluted from the column using 30 mM Sodium Phosphate, 200 mM NaCl, pH 7.2. Collection begins when the conductivity rises sharply (to >4 mS/cm) and the UV rises above 0.5 AU. Collection ends when UV returns to 0.2 AU. The volume of the eluate should be approximately 2–3 CV's at an angiostatin concentration of 3.3 g/L of eluate.

The column is regenerated using 7 column volumes (CV's) of 2M NaCl. The 2M NaCl Regeneration is followed with 6M Urea. After an initial Urea Wash, Urea is recirculated for a minimum of 1 hour. The Urea dissolves the cell paste and eases removal of the cell paste from the column. The regeneration is followed with a WPU flush until the UV returns to baseline.

The column is sanitized with 0.5M NaOH then stored in 0.1M NaOH. The 0.1 M NaOH may be prepared inline by mixing 0.5M NaOH and WPU so that the inlet conductivity is 23±5 mS/cm.

SEPHAROSE® FF and Ceramic Hydroxyapatite Chromatography

The Q SEPHAROSE® (ion exchange) column (30 cm×15 cm column, 10.61, CV) and Ceramic Hydroxyapatite (CHT) column (45 cm×37 cm column, 58.8L CV) which were stored in 0.1M NaOH are rinsed with 5CV's of 10 mM Sodium Phosphate, pH 7.0. The maximum flowrate for this chromatography is 480LPH (300 cm/hr of CHT Column) and is performed at ambient temperature. The angiostatin flows through the Q SEPHAROSE® (ion exchange) column and binds to the CHT column. The columns are charged with 0.5M Sodium Phosphate, pH 7.0 then equilibrated with 10 mM Sodium Phosphate, pH 7.0 until the pH and conductivity are that of the equilibration buffer. The elution from the STREAMLINE® SP Chromatography of Angiostatin is diluted inline with WFI (1 part elution: 3 part WFI and loaded onto the column. The column is washed to baseline with 10 mM Sodium Phosphate, pH 7.0. The Q SEPHAROSE® (ion exchange) column is removed from the chromatography skid.

The angiostatin is eluted from the CHT column with a 5CV linear gradient from 10 mM Sodium Phosphate, pH 7.0 to 74 mM Sodium Phosphate, pH 7.0. The 74 mM Sodium Phosphate, pH 7.0 is continued until the UV returns to <0.5 AU. The product is collected from peak beginning at 0.15 AU to peak ending at 0.3 AU. The volume of the elution should be approximately 6–8 CV's at an angiostatin concentration of ~0.8 g/L.

The CHT column is regenerated with 0.5M Sodium Phosphate, pH 7.0. The Q SEPHAROSE® FF column is regenerated with 2M NaCl. The columns are then cleaned with 0.5M NaOH and held for at least 1 hour (maximum of 24 hours). The columns are then stored in 0.1M NaOH which is prepared by blending 0.5M NaQH and WFI.

TOYOPEARL® Phenyl 650M Chromatography

The TOYOPEARL® Phenyl 650M (hydrophobic interaction resin Column (45 cm×25 cm column, 40L CV) which was stored in 0.1M NaOH is rinsed with WFI until neutral conditions have been met. The flowrate for this chromatography is 480LPH (300 cm/hr) and is performed at ambient temperature. The column is equilibrated with 50 mM Sodium Phosphate, 24 mM Citric Acid, 1.4M Ammonium Sulfate, pH 5.1 until the pH and conductivity are that of the equilibration buffer.

The elution from the CHT column is diluted inline with 50 mM Sodium Phosphate, 24 mM Citric Acid, 2.8M Ammonium Sulfate, pH 4.5 (1 part elution: 1 part buffer) and loaded onto the TOYOPEARL® 650M column. The loaded column is then washed with 50 mM Sodium Phosphate, 24 mM Citric Acid, 1.4M Ammonium Sulfate, pH 5.1. The angiostatin is eluted from the column using a 20CV linear gradient from 50 mM Sodium Phosphate, 24 mM Citric Acid, 1.4M Ammonium Sulfate, pH 5.1 to 50 mM Sodium Phosphate, 24 mM Citric Acid, 0.92M Ammonium Sulfate, pH 5.1. The 50 mM Sodium Phosphate, 24 mM Citric Acid, 0.92M Ammonium Sulfate is continued until UV returns to <0.1 AU. The eluate is collected from peak beginning at 0.3 AU to peak ending at 0.1 AU. The elution volume is approximately 8CV's at an angiostatin concentration of ~0.7 g/L. The column is regenerated with 50 mM Sodium Phosphate, 24 mM Citric Acid, pH 5.1. The column is rinsed with WFI and then cleaned with 0.5M NaOH. The column is then stored in 0.1M NaOH which may be prepared by blending 0.5M NaGH inline with WFI. Note: If the TOYOPEARL® Phenyl Elution will not be processed within 8 hours, the elution is to be diluted 1× with WFI and stored at 2–8° C. for a maximum of 48 hours.

The Ultrafiltration/Diafiltration steps are described in greater detail in the following paragraphs.

100 sq. feet of 5Kd polyethersulfone filters are sanitized with 0.5M NaOH and held in 0.5M NaOH for a minimum of 1 hour (maximum of 2 hours). The filters are then rinsed with WFI until neutral conditions are obtained. The filters are then equilibrated with 0.15M Sodium Chloride until the retentate pH and conductivity is that of the equilibration buffer. The TOYOPEARL® Elution (if not diluted) is diafiltered 1×with 0.15M Sodium Chloride. The Diafiltered product is concentrated to 5 mg/mL then diafiltered again until the pH and conductivity is that of the formulation buffer (~7 volumes). The UF/DF skid is rinsed with 2×10L flushes which are added to the diafiltered product. Due to the hold up volume of the UF/DF skid, it is necessary to perform the final concentration on a table top unit with 25 sq. feet of filter. The retentate is then concentrated to 20.0 mg/mL. The UF/DF filters are rinsed with 0.15M Sodium Chloride and the rinse is added to the concentrated product. The UF/DF retentate is adjusted with 0.15M Sodium Chloride to a final concentration of 15 mg/ml. Note: If the TOYOPEARL® Elution was diluted the 1×diafiltration may be omitted.

Formulation

The formulated pool is then aseptically filtered through a 0.2 micron filter. The filtered angiostatin is bulk filled into sterile bottles and then stored at ~70° C.

This invention is further illustrated by the following examples, which are not to be construed in any way as imposing limitations upon the scope thereof. These conditions for angiostatin protein production and/or purification may be scaled up, for example, by 5, 10, 20 or 100 fold to accommodate the need for large scale angiostatin protein production. On the contrary, it is to be clearly understood that resort may be had to various other embodiments, modifications, and equivalents thereof. which, after reading the description herein, may suggest themselves to those skilled in the art without departing from the spirit of the present invention.

EXAMPLE 1

Sequence of Human Angiostatin Protein

The following is an example of a functional human angiostatin protein of the present invention. This is the angiostatin protein amino acid sequence encoded by the gene sequence listed below as SEQ ID NO: 1.

ANGIOSTATIN Production Clone ENMA98: Angiostatin gene and protein sequences. SEQ ID NO:1 shows the amino acid sequence of the angiostatin protein produced from the production clone ENMA98 which contains the nucleotide sequence shown in SEQ ID NO:2 hASv3 protein sequence (260 aa)
VYLSECKTGNGKNYRGTMSKTKNGITCQKWSSTSPHRPR SEQ ID NO:1

FSPATHPSEGLEENYCRNPDNDPQGPWCYTTDPEKRYDY

CDILECEEECMHCSGENYDGKISKTMSGLECQAWDSQSP

HAHGYIPSKFPNKNLKKNYCRNPDRELRPWCFTTDPNKR

WELCDIPRCTTPPPSSGPTYQCLKGTGENYRGNVAVTVS

GHTCQHWSAQTPHTHERTPENFPCKNLDENYCRNPDGKR

APWCHTTNSQVRWEYCKIPSCDSSPV hASv3 DNA sequence (780 bp)
GTGTATCTCTCAGAGTGCAAGACTGGGAATGGAAAGAAT SEQ ID NO:2

TACAGAGGGACGATGTCCAAAACAAAAAATGGCATCACC

TGTCAAAAATGGAGTTCCACTTCTCCCCACAGACCTAGA

TTCTCACCTGCTACACACCCCTCAGAGGGACTGGAGGAG

AACTACTGCAGGAATCCAGACAACGATCCGCAGGGGCCC

TGGTGCTATACTACTGATCCAGAAAAGAGATATGACTAC

TGCGACATTCTTGAGTGTGAAGAGGAATGTATGCATTGC

AGTGGAGAAAACTATGACGGCAAAATTTCCAAGACCATG

TCTGGACTGGAATGCCAGGCCTGGGACTCTCAGAGCCCA

-continued

CACGCTCATGGATACATTCCTTCCAAATTTCCAAACAAG

AACCTGAAGAAGAATTACTGTCGTAACCCCGATAGGGAG

CTGCGGCCTTGGTGTTTCACCACCGACCCCAACAAGCGC

TGGGAACTTTGTGACATCCCCCGCTGCACAACACCTCCA

CCATCTTCTGGTCCCACCTACCAGTGTCTGAAGGGAACA

GGTGAAAACTATCGCGGGAATGTGGCTGTTACCGTGTCC

GGGCACACCTGTCAGCACTGGAGTGCACAGACCCCTCAC

ACACATGAAAGGACACCAGAAAACTTCCCCTGCAAAAAT

TTGGATGAAAACTACTGCCGCAATCCTGACGGAAAAAGG

GCCCCATGGTGCCATACAACCAACAGCCAAGTGCGGTGG

GAGTACTGTAAGATACCGTCCTGTGACTCCTCCCCAGTA

There is only one amino acid change (Asn-->Glu) in the protein sequence comparing to the wild type plasminogen K1-3, and one codon change in the nucleotide sequence (AAC-->GAA) corresponding to angiostatin protein.

EXAMPLE 2

Details Concerning Chromatography, Diafiltration/Ultrafiltration, Bulk Formulation and Various Buffers used in the Procedure for Purification of ANGIOSTATIN Protein

| | |
|---|---|
| STREAMLINE ® SP Chromatography (cation-exchange resin) Column Specifications | |
| Resin: | STREAMLINE ® SP |
| Type: | Expanded Bed Adsorption |
| Particle Size: | 200 micron |
| Dimensions: | 60 cm x 18 cm, 51 L Resin, expanded bed volume ~150 L, expanded bed height of ~54 cm at 848 LPH |
| Pressure: Limitation: | 2.0 bar |
| Expected Flowrate: Sanitization and Rinse | 848 LPH (660–740 LPH for load and wash) |
| Buffer: | 0.5 M NaOH |
| Approximate Volume Required | 7 CV (357 L) |
| Flow Direction: | Up |
| Hold Time: | Minimum of 6 hours (maximum of 24 hours) |
| WPU Rinse: Equilibration | Until conductivity <1.0 mS/cm |
| Buffer: | 50 mM Sodium Phosphate, 24 mM Citric Acid, pH 5.1 |
| Approximate Volume Required: | 14 CV (714 L) |
| Flow Direction: | Up |
| Equilibration Specifics: Load | Conductivity 5.5–6.5 mS/cm PH = 5.1 ± 0.2 |
| Capacity: | > unknown at this time mg/mL |
| Load Conductivity: | 9–12 mS/cm |
| WFI Dilution: | ~3 volumes of WPU |
| Flow Direction: | Up |
| Loading Time: | ~5.5 hours |
| Volume of Load: | ~4500 L |

-continued

Wash

| | |
|---|---|
| Buffer: | 15% Glycerol, 15 mM Sodium Phosphate, pH 6.1 |
| Approximate Volume Required: | 14 CV (714 L) |
| Flow Direction: | Up then down (12 cv up/2 cv down) |
| Wash Specifics: | Conductivity <1.5 mS/cm |
| | pH = 6.1 ± 0.2 |

Elution

| | |
|---|---|
| Type: | Step Elution |
| Buffer: | 30 mM Sodium Phosphate, 200 mM NaCl, pH 7.2. |
| Approximate Volume Required: | 11 CV (561 L) |
| Flow Direction: | Down |
| Elution Specifics: | Collection begins UV >0.5 AU and Conductivity >6 mS/cm Angiostatin Concentration 2.5–3.3 g/L |
| Approximate Eluate Volume: | 2–3 CV |
| Product Storage Conditions: | Ambient (<8 hours) 2–8° C. (<24 hours) |
| Product Testing: | LAL and UV |

Regeneration #1

| | |
|---|---|
| Buffer: | 2 M NaCl |
| Approximate Volume Required: | 7 CV (357 L) |
| Flow Direction: | Up |

Regeneration #2 and Rinse

| | |
|---|---|
| Buffer: | 6 M Urea |
| Approximate Volume Required: | 10 CV Total (510 L) |
| Flow Direction: | Up for 8 CV (408 L). Recirculate down with 2 CV (100 L) for 60 minutes |
| WPU Rinse: | Until UV return to baseline |

Cleaning

| | |
|---|---|
| Buffer: | 0.5 M NaOH |
| Approximate Volume Required: | 7 CV (357 L) |
| Flow Direction: | Up |
| Hold Time: | Minimum 1 hour (maximum of 24 hours) |

Storage

| | |
|---|---|
| Buffer: | 0.1 M NaOH (inline dilution 0.5 M NaOH/WPU) |
| Approximate Volume Required: | 7 CV (357 L total, 71 L 0.5 M NaOH) |
| Flow Direction: | Down |

Purification
General Purification

| | |
|---|---|
| Storage Conditions: | Storage >8 hours at 2–8° C. No stability data has been generated. Therefore, storage time should be limited to less than 24 hours. Final product storage is −70° C., |
| Extinction Coefficient: | 2.08 |
| Shear Sensitivity: | Not Determined |
| Concentration Limit: | Not Determined |
| In process Testing | LAL, UV, PD and QC retains |

SEPHAROSE ® (ion exchange) and
Ceramic Hydroxyapatite Chromatography
Column Specifications

| | |
|---|---|
| Resin: | SEPHAROSE ® FF (Pharmacia) |
| Type: | Ion Exchange (Flowthrough) |
| Particle Size: | 90 micron |
| Dimensions: | 30 cm D x 15 cm H 1 O.GL CV |
| Pressure Limitation: | 3.0 bar |
| Expected Flowrate: | 480 LPH |
| Resin: | Ceramic Hydroxyapatite (Biorad) |
| Type: | Mixed Mode |
| Particle Size: | 40 micron |
| Dimensions: | 45 cm D x 37 cm H 58 L CV |
| Pressure Limitation: | 2.5 bar |
| Expected Flowrate: | 480 LPH |

-continued

Rinse

| | |
|---|---|
| Buffer: | 10 mM Sodium Phosphate, pH 7.0 |
| Specifics: | Rinse until conductivity <3.0 mS/cm |

Charge

| | |
|---|---|
| Buffer: | 0.5 M Sodium Phosphate, pH 7.0 |
| Approximate Volume Required: | 3 CV (175 L) |
| Flow Direction: | Up |

Equilibration

| | |
|---|---|
| Buffer: | 10 mM Sodium Phosphate, pH 7.0 |
| Approximate Volume Required: | 5–7 CV (292–408 L) |
| Flow Direction: | Up |
| Equilibration Specifics: | pH = 7.0 ± 0.1<br>Conductivity = 1.0–1.6 mS/cm |

Load

| | |
|---|---|
| Capacity: | 6–13 mg/mL |
| Conductivity: | 4–6 mS/cm |
| WFI Dilution: | 3 Volumes Inline |
| Flow Direction: | Up |
| Loading Time: | 1.5 hr |
| Volume of Load: | 600 L (4x STREAMLINE ® Elution) |

Wash

| | |
|---|---|
| Buffer: | 10 mM Sodium Phosphate, pH 7.0 |
| Approximate Volume Required: | 3 CV (175 L) |
| Flow Direction: | Up |
| Wash Specifics: | pH = 7.0 ± 0.2 |

Elution (from CHT)

| | |
|---|---|
| Type: | Linear Gradient 0 to 100% (A to B) |
| Buffer A: | 10 mM Sodium Phosphate, pH 7.0 |
| Buffer B: | 74 mM Sodium Phosphate, pH 7.0 |
| Approximate Volume Required: | SCV (239 L) Hold in B for SCV (239 L) |
| Flow Direction: | Up |
| Product Collection: | Start @ 0.15 AU pre Peak and end @ 0.3 AU post Peak |
| Elution Specifics: | pH = 7.0 ± 0.2<br>Volume - 4-S CV<br>Angiostatin ® concentration ~0.8 mg/mL |

Regeneration of CHT Column

| | |
|---|---|
| Buffer: | 0.5 M Sodium Phosphate, pH 7.0 |
| Approximate Volume Required: | 3 CV (143 L) |
| Flow Direction: | Down |

Regeneration of Q SEPHAROSE ® Column

| | |
|---|---|
| Buffer: | 2 M NaCl |
| Approximate Volume Required: | 3 CV (32 L) |
| Flow Direction: | Down |

Cleaning (both columns)

| | |
|---|---|
| Buffer: | 0.5 M NaOH |
| Approximate Volume Required: | SCV (292 L) |
| Flow Direction: | Down |
| Hold Time: | Minimum 1 hour (Maximum of 24 hours) |

Storage

| | |
|---|---|
| Buffer: | 0.1 M NaOH |
| Approximate Volume Required: | 3 CV (175 L) |
| Flow Direction: | Down |

TOYOPEARL ® Phenyl 650 M Chromatography

TOYOPEARL ® Phenyl 650 M Column (hydrophobic interaction resin)

-continued

| Specifications | |
|---|---|
| Resin: | TOYOPEARL ® Phenyl 650 M (TosoHaas) |
| Type: | Hydrophobic Interaction |
| Particle Size: | 65 micron |
| Dimensions: | 45 cm D x 25 cm H 40 L CV |
| Pressure Limitation: | 2.5 bar |
| Expected Flowrate: | 480 LPH |

Rinse

| | |
|---|---|
| WFI Rinse: | Until conductivity <1.0 MS/cm |
| Rinse Specifics: | Perform a 3 CV gradient from O.1 M NaOH to WFI then continue rinsing |
| Flow Direction: | Up |

Equilibration

| | |
|---|---|
| Buffer: | 50 mM Sodium Phosphate, 24 mM Citric Acid, 1.4 M Ammonium Sulfate, pH 5.1 |
| Transition Specific: | Perform a 3 CV gradient from WFI to EQ buffer the continue with equilibration |
| Approximate Volume Required: | 4.5 CV (180 L) |
| Flow Direction: | Up |
| Equilibration Conductivity 154–171 mS/cm Specifics: | Density = 1.10 Kg/L |

Load

| | |
|---|---|
| Capacity: | >12 mg/mL |
| Conductivity: | 154–171 mS/cm |
| Buffer Dilution: | 1x (50 mM Sodium Phosphate, 24 mM Citric Acid, 2.8 M Ammonium Sulfate, pH 4.6) |
| Volume Buffer Required: | ~350 L |
| Flow Direction: | Up |
| Loading Time: | 1.25 hr |
| Volume of Load: | ~700 L |

Wash

| | |
|---|---|
| Buffer: | 50 mM Sodium Phosphate, 24 mM Citric Acid, 1.4 M Ammonium Sulfate, pH 5.1 |
| Approximate Volume Required: | IOCV (400 L) |
| Flow Direction: | Up |
| Wash Specifics: | Conductivity = 154–171 mS/cm pH = 5.1 ± 0.2 |

Elution

| | |
|---|---|
| Type: | Linear Gradient from 0 to 100% (A to B), Hold in B for 5 CV |
| Buffer A: | 50 mM Sodium Phosphate, 24 mM Citric Acid, 1.4 M Ammonium Sulfate, pH 5.1 |
| Buffer B: | 50 mM Sodium Phosphate, 24 mM Citric Acid, 0.92 M Ammonium Sulfate, pH 5.1 |
| Approximate Volume Required: | 20 CV (800 L) Hold for 5 CV (200 L) B |
| Flow Direction: | Up |
| Product Collection: | Start @ 0.3 AU pre Peak and end @ 0.1 AU post Peak |
| Elution Specifics: | Eluate Volume ~8 CV's Angiostatin Concentration - 0.6 g/L |

Regeneration

| | |
|---|---|
| Buffer: | 50 mM Sodium Phosphate, 24 mM Citric Acid, pH 5.1 |
| Approximate Volume Required: | 3 CV (120 L) |
| Flow Direction: | Down |
| WFI Rinse: | ~3 CV |

Cleaning

| | |
|---|---|
| Buffer: | 0.5 M NaOH |
| Approximate Volume Required: | 4 CV (160 L) |
| Flow Direction: | Down |
| Hold Time: | Minimum 1 hour (Maximum of 24 hours) |

Storage

| | |
|---|---|
| Buffer: | 0.1 M NaOH |
| Approximate Volume Required: | 5 CV (200 L) |

-continued

| | |
|---|---|
| Flow Direction: | Down |
| UF/DF Filter Specifications | |
| Skid: | OF Skid (25–45 LPM flowrate) and Table Top Unit (5–10 LPM) |
| Membrane: | 5 Kd Polyethersulfone |
| Membrane area: | 100 sq. ft. (Skid) 25 sq. ft. (Table Top) |
| Recirculation rate: | 25–45 L/min (Skid) 5–10 L/min (Table Top) |
| Expected Flux rate: | ~10 L/min (Skid) ~1 L/min (Table Top) |
| Feed Pressure Range: | 10–25 psi (Skid) 5–10 psi (Table Top) |
| TMP Range: | 10–20 psi (Skid) 5–10 psi (Table Top) |
| Equilibration | |
| Buffer: | 0.15 M Sodium Chloride |
| Approximate Volume Required: | 500 L |
| Equilibration Specifics: | Conductivity - 12–14 mS/cm a 18–22° C. |
| Initial Diafiltration | |
| Buffer: | 0.15 M Sodium Chloride |
| Approximate Volume Required: | 1 DV (400 L) |
| Initial Concentration | |
| Starting Concentration: | 0.6 g/L |
| Approximate Starting Volume: | 330 L |
| Intermediate Concentration: | 5 g/L |
| Approximate Final Volume: | 30 L |
| Approximate Concentration Factor: | 8 |
| Final Diafiltration | |
| Buffer: | 0.15 M Sodium Chloride |
| Diafiltration Specifics | Until pH and conductivity are that of the 0.15 M Sodium Chloride |
| Approximate Volume Required: | 7 DV (280 L) |
| Rinse of UF/DF Skid | |
| Buffer: | 0.15 M Sodium Chloride |
| Approximate Volume Required: | 2 x 1 OL Flushes |
| Washout Specifics: | Add both flushes to product tank |
| Final Concentration (Performed on Table Top Unit) | |
| Starting Concentration: | 3 g/L |
| Approximate Starting Volume: | 45 L |
| Intermediate Concentration: | 20 g/L |
| Approximate Final Volume: | 10 L |
| Approximate Concentration Factor: | 4 |
| Rinse of Table Top Unit | |
| Buffer: | O.15 M Sodium Chloride |
| Approximate Volume Required: | <_31, |
| Washout specifics: | Transfer all of rinse to the concentrated product |
| Dilution (May not be required) | |
| Initial | 15.4 mg/mL |

-continued

| | |
|---|---|
| Concentration: | |
| Approximate Initial Volume: | 13 L |
| Final Concentration: | 15.0 mg/mL |
| Approximate Final Volume: | 13.3 L |
| Buffer: | 0.1 SM Sodium Chloride |
| Approximate Volume Required: | 0.3 L |

Angiostatin Formulated Bulk
Bulk Filling
Specifics

| | |
|---|---|
| Bottle Type: | PETG |
| Size: | 1 L |
| Fill per bottle: | 800 mL |
| Total # of bottles: | 25 |

Release Testing

| | |
|---|---|
| Quality - Appearance | Clear, colorless to slightly pink |
| Quality - Osmolality | Report |
| Purity - Size Exclusion HPLC | Report |
| Strength - UV Absorbance | 10–20 mg = mL (based on 1 mg/mL = 2.08 AU '@ 280 nm) |
| Identity - SDS-Page (non-reduced) | Corresponds to reference |
| Safety - DNA Threshold | Report |
| Safety - LAL | $\geq$0.50 EU/mg |
| Safety - Bioburden | $\geq$10 CFU/mL |

Buffer Preparation
General Buffer Preparation

| | |
|---|---|
| Specifics: | Buffers made by volume 21 day expiration on all buffers (based on safety) |
| In Process Testing: | pH and Conductivity (measured @ 18–22° C.) Density for STREAMLINE ® Wash Buffer and Phenyl Buffers |
| QC Testing: | LAL and Bioburden |

50 mM Sodium Phosphate, 24 mM Citric Acid, pH 5.1

| | | |
|---|---|---|
| Unit Description: | Op STREAMLINE ® Equilibration and TOYOPEARL ® 650 M Regeneration | |
| Component and Concentration: | Sodium Phosphate, Dibasic | 13.4 g/L |
| | Citric Acid, Monohydrate | 5.04 g/L |
| pH Adjustment | NaOH or HCl | TBD |
| Conductivity: | 5–7 mS/cm | |
| pH: | 4.9–5.3 | |
| Density: | 1.00 Kg/L | |

30 mM Sodium Phosphate, 200 mM NaCl, pH 7.2

| | | |
|---|---|---|
| Unit Description: | Op STREAMLINE ® Elution | |
| Component and Concentration: | Sodium Phosphate, Dibasic | 6.40 g/L |
| | Sodium Phosphate, Monobasic | 0.846 g/L |
| | Sodium Chloride | 11.69 g/L |
| pH Adjustment | NaOH or HCl | TBD |
| Conductivity: | 19–23 mS/cm | |
| pH: | 7.0–7.4 | |
| Density: | 1.00 Kg/L | |

15% Glycerol, 15 mM Sodium Phosphate, pH 6.1

| | | |
|---|---|---|
| Unit Description: | Op STREAMLINE ® Wash | |
| Component and Concentration: | Glycerol | 189 g/L (15% v/v) |
| | Sodium Phosphate, Dibasic | 0.7 g/L |
| | Sodium Phosphate, Monobasic | 2.08 g/L |
| pH Adjustment | NaOH or HCl | TBD |
| Conductivity: | <1.5 mS/cm | |
| pH: | 5.9–6.3 | |
| Density: | ~1.04 Kg/L | |

10 mM Sodium Phosphate, pH 7.0

| | | |
|---|---|---|
| Unit Description: | Op Q SEPHAROSE ® and CHT Equilibration/Wash/Elution | |
| Component and Concentration: | Sodium Phosphate, Dibasic | 1.63 g/L |
| | Sodium Phosphate, Monobasic | 0.54 g/L |
| pH Adjustment | NaOH or HCl | TBD |
| Conductivity: | 1.0–1.6 mS/cm | |
| pH: | 6.9–7.1 | |

-continued

| | | |
|---|---|---|
| Density: | 1.00 Kg/L | |
| 74 mM Sodium Phosphate, pH 7.0 | | |
| | | |
| Unit Description: | Op Q SEPHAROSE ® and CHT Elution | |
| Component and | Sodium Phosphate, Dibasic | 12.1 g/L |
| Concentration: | Sodium Phosphate, Monobasic | 3.98 g/L |
| pH Adjustment | NaOH or HCl | TBD |
| Conductivity: | 6.0–7.2 mS/cm | |
| pH: | 6.9–7.1 | |
| Density: | 1.00 Kg/L | |
| O.5 M Sodium Phosphate, pH 7.0 | | |
| | | |
| Unit Description: | Op Q SEPHAROSE ® and CHT Regeneration | |
| Component and | Sodium Phosphate, Dibasic | 81.8 g/L |
| Concentration: | Sodium Phosphate, Monobasic | 26.9 g/L |
| pH Adjustment: | NaOH or Phosphoric Acid | TBD |
| Conductivity: | 35–41 mS/cm @ 18–20° C. | |
| pH: | 6.9–7.1 | |
| Density: | 1.00 Kg/L | |
| 50 mM Sodium Phosphate, 24 mM Citric Acid, | | |
| 1.4 M Ammonium Sulfate, pH S._1 | | |
| | | |
| Unit Description: | Op TOYOPEARL ® 650 M Equilibration/Wash/Elution | |
| Component and | Sodium Phosphate, Dibasic | 13.4 g/L |
| Concentration: | Citric Acid | 5.04 g/L |
| | Ammonium Sulfate | 185.0 g/L |
| pH Adjustment: | NaOH or HCl | |
| Conductivity: | 206–228 mS/cm | |
| pH: | 4.9–5.3 | |
| Density: | 1.092–1.112 Kg/L | |
| 50 mM Sodium Phosphate, 24 mM Citric Acid, | | |
| 0.92 M Ammonium Sulfate, pH 5.1 | | |
| | | |
| Unit Description: | Op. TOYOPEARL ® 650 M Elution | |
| Component and | Sodium Phosphate, Dibasic | 13.4 g/L |
| Concentration: | Citric Acid, Monohydrate | 5.04 g/L |
| | Ammonium Sulfate | 121.6 g/L |
| pH Adjustment: | NaOH or HCl | TBD |
| Conductivity: | 156–173 mS/cm | |
| pH: | 4.9–5.3 | |
| Density: | 1.068–1.084 g/L | |
| 50 mM Sodium Phosphate, 24 mM Citric Acid, | | |
| 2.8 M Ammonium Sulfate, pH 4.5 | | |
| | | |
| Unit Description: | Op TOYOPEARL ® 650 M Load Dilution | |
| Component and | Sodium Phosphate, Dibasic | 13.4 g/L |
| Concentration: | Citric Acid, Monohydrate | 5.04 g/L |
| | Ammonium Sulfate | 370 g/L |
| pH Adjustment: | NaOH or HCl | TBD |
| Conductivity: | 359–357 mS/cm | |
| pH: | 4.3–4.7 | |
| Density: | 1.167–1.204 Kg/L | |
| Formulation Buffer (0.15 M NaCl) | | |
| | | |
| Unit Op Description: | O/DF Diafiltration Buffer | |
| Component and Concentration: | Sodium Chloride 8.76 g/L | |
| Conductivity: | 12–14 mS/cm | |
| Density: | 1.00 Kg/L | |

EXAMPLE 3

Biochemical characterization verified the identity of the purified protein as human ANGIOSTATIN® and indicated that the protein was over 95% pure. The initial step in purification, hydrophobic interaction chromatography (HIC), removed the majority of pigments and extraneous proteins; yielding 80–90% pure ANGIOSTATIN®. A number of resins and buffer systems were examined for ANGIOSTATIN® binding capacity and specificity. The binding capacity of ANGIOSTATIN® protein to TOYOPEARL® Phenyl 650m (TosoHaas) was 20–30% higher than the binding capacity of Phenyl SEPHROSE® high sub (Pharmacia) in PBS containing 3.0 M NaCl. At pH 7.4, a buffer system utilizing sodium chloride dramatically increased the binding specificity of Phenyl 650m for ANGIOSTATIN® versus an Ammonium Sulfate buffer system.

EXAMPLE 4

ANGIOSTATIN© Purity and Identification of Glycosylation Site

Purification of ANGIOSTATIN© protein results in one major species as well as a number of minor species which can be separated by reverse phase chromatography and SDS-PAGE. Western blot analysis using a polyclonal primary antibody indicated that all minor species were related to the major intact angiostatin protein. Electrospray ionization mass spectrometry of the reduced protein detected two major components whose deconvoluted spectra indicated masses of 29788 Da and 29951 Da., consistent with an intact angiostatin molecule and an intact molecule with a single hexose sugar (+163 Da), respectively. Digestion of the molecule with lysyl endopeptidase followed by LC-MS indicated this modification is localized to Kringle domain 1 (residues 30–74). Analysis of a trypsin subdigest of this peptide by LC/MS/MS demonstrated that this sugar is linked to Serine 31. This was confirmed by N-terminal sequencing.

The peptide map and N-terminal sequencing were also useful in identifying an additional glycosylation site and minor cleavage products of the angiostatin molecule.

All patents, publications and abstracts cited above are incorporated herein by reference in their entirety.

The invention has been described in detail with particular reference to certain embodiments, but variations and modifications can be made without departing from the spirit and the scope of the present invention.

What is claimed is:

1. A method for purifying recombinantly produced angiostatin comprising:

applying crude fermentation broth containing the recombinantly produced angiostatin to an expanded bed cation exchange column;

collecting eluate from the expanded bed cation exchange column and applying the eluate from the expanded bed cation exchange column to an anion exchange column;

collecting eluate from the anion exchange column and applying the eluate from the anion exchange column to a hydroxyapatite column;

collecting eluate from the hydroxyapatite column and applying the eluate from the hydroxyapatite column to a hydrophobic column;

collecting eluate from the hydrophobic column and applying the eluate from the hydrophobic column to a membrane; and, collecting fluid passing through the membrane.

2. The method of claim 1 further comprising:

concentrating the fluid;

diafiltering the fluid;

concentrating the diaflitered fluid; and passing the concentrated and diafiltered fluid through a second membrane.

3. The method of claim 2, further comprising:

collecting fluid passing through the second membrane;

concentrating the fluid passing through the second membrane; and aseptically filtering the concentrated fluid.

4. The method of claim 1, wherein the recombinantly produced angiostatin is human angiostatin.

5. The method of claim 4, wherein the recombinantly produced human angiostatin is produced from fermentation of Pichia pastoris.

6. The method of claim 1, wherein the crude fermentation broth containing the recombinantly produced angiostatin is applied to the expanded bed cation exchange column in an upward direction, followed by application of elution buffer and elution of the column in a downward direction.

* * * * *